United States Patent [19]

Wilson

[11] Plant 4,652

[45] Feb. 17, 1981

[54] PEACH TREE

[75] Inventor: William J. Wilson, Fort Valley, Ga.

[73] Assignee: Bountiful Ridge Nurseries, Inc., Princess Anne, Md.

[21] Appl. No.: 109,608

[22] Filed: Jan. 4, 1980

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Frank B. Robb

[57] ABSTRACT

A Peach Tree developed from a seedling growing in planting of "Rio-Oso-Gem" (U.S. Plant Pat. No. 84) reproduced asexually, having characteristics of the female parent, the male parent not being known, the tree having large and vigorous, tall, vase formed, with leaves larger than "Rio-Oso-Gem", heavy setting requiring heavy thinning to properly size the fruit, the symmetrical almost globular fruit of reddish overall appearance with some mottling and yellow ground color, varying between 35-12 and 35-13, with areas of 35-5, with the flesh having yellowish portions 27-4, areas of 35-5 depending upon the angle of light availed of for observation.

1 Drawing Figure

The present invention relates to a new and distinct variety of Peach Tree of yellowish fleshed, freestone, fruit bearing type, which was originated by me as an open pollinated selection from plantings of "Rio-Oso-Gem" (U.S. Plant Pat. No. 84) having a number of characteristics which distinguish the same from Rio-Oso-Gem particularly the non-browning of the fruit, resistance to bacterial spot and more nearly globular symmetrical fruit.

Further the flowers of my new variety reach full bloom somewhat later and are of a larger size than those of Rio-Oso-Gem.

My new variety has substantially less prominent ridge along the line of suture than Rio-Oso-Gem.

A consideration of the bloom of my new variety discloses that the same is more showy than Rio-Oso-Gem having an almost red center with petals more lavender, when viewed as an entire flower but as individual petals are separated the lighter effect is noted when they are viewed separately.

The leaves of my new variety, which I call "Jim Wilson" and have likewise designated in my records as W-750, are also somewhat larger than Rio-Oso-Gem, being about 1¾" wide and 7" long, although they are somewhat wavy as those of Rio-Oso-Gem.

The fruit of my new variety is not as elongated as Rio-Oso-Gem being more nearly globular and thus very symmetrical.

The fruit further presents a brighter reddish overall color effect with some mottling and a yellow ground color but the fruit does not have the black almost crimson ground color of Rio-Oso-Gem, and is in fact quite different in overall appearance.

I have caused my new variety to be asexually reproduced at my orchard near Fort Valley, Ga. by budding and find that it comes true in succeeding generations with propagations, and with like characteristics. My new peach variety has also been asexually reproduced near Princess Anne, Md., and likewise retains the herein described characteristics, it appearing that the fruit characteristics detailed here are very closely maintained under the conditions existing at both Princess Anne and at Fort Valley, Ga., suggesting that a wide variety of locations for growth do not disturb the desirable attributes likewise here detailed.

The fruit of my new variety is available at a time between the ripening of "Red Haven" and "Loring", thus making it a good commercial variety.

The accompanying drawing shows typical specimens of the fruit and flower of my new variety, with the fruit being illustrated in both elevation and in cross-section, all being depicted in color as nearly true as it is reasonably possible to make the same in a color illustration of this character, and as viewed in like conditions, to illustrate both color and suggest shape and texture likewise.

It is noted however that the leaves that appear in the flower illustration, are somewhat different from the true color because of the photographic process resorted to herein.

There follows a detailed description of my new variety of peach tree, with color terminology designated in accordance with Munsell Color Cascade published by MacBeth Division of Kollmorgen Corporation, and certain color terms being adopted as suitable to denote the color, some of them having ordinary dictionary significance where the same is appropriate:

Parentage: Open-pollinated seed from plantings of "Rio-Oso-Gem".

Locality where grown and observed: Near Fort Valley, Ga.

Dates of first and last pickings: July 22 to August 1.

Tree: Large size; vigorous; spreading; tall; vase formed; rapid growing; hardy; very productive; regular bearer.

*Trunk.*—Stocky; smooth.

*Branches.*—Smooth. Color — red to brown.

*Leaves.*—Wide and long; large; smooth. Length — about 7 inches. Width — about 1¾ inches. Form — ovate; taper pointed; medium. Color — dark green — top 16-8; bottom 17-6. Margin — glandular; finely serrate. Petiole — medium length — ½".

Flowers:

*Dates of first and full bloom.*—End of March to first of April.

*Size.*—Large — about 2 inches in diameter.

Fruit:

*Maturity when described.*—Late July.

*Size.*—Uniform. Axial diameter — about $2\frac{7}{8}$ inches. Transverse diameter — about $3\frac{1}{4}$ inches.

*Form.*—Uniform; symmetrical; regular; globose; ribbed.

*Cavity.*—Symmetrical; abrupt at base. Depth — $\frac{5}{8}$ inches. Breadth — about 1 inch.

*Basin.*—Abrupt; narrow; even; pubescent.

*Stem.*—Stout; glabrous. Length — $\frac{3}{8}$ inches. Bracts — wanting.

*Skin.*—Thick; tough; smooth. Ground color — yellow 26-4. Color effect — reddish 35-12 to 35-13 with yellow ground color.

*Flesh.*—Juicy. Color — yellowish 27-4.

*Texture.*—Melting.

*Flavor.*—Sweet; rich; aroma-pronounced. Tends to color early though not ready to be picked until suture smooths out.

Use: Local; dessert; and culinary.

Keeping quality: Good; about three weeks in ordinary storage conditions.

Resistance to disease: Good; particularly resistant to bacterial spot and definitely non-browning.

I claim:

1. A new and distinct variety of peach tree of the yellow-fleshed, freestone, fruit-bearing type, substantially as herein shown and described, characterized particularly as to novelty by the unique combination of large tree size, tall, vase formed and rapid growing, tendency to set fruit heavy requiring heavy thinning to properly size fruit, the fruit being very uniform in size, and more nearly globular than "Rio Oso Gem", more symmetrical with thick skin, smooth and tough, the overall color presenting a reddish general appearance from 35-12 to 35-13 and shading to 35-5 with some mottling over a yellow ground color, the early tendency to color, though picking must be delayed until the suture smooths, the pronounced aroma of the fruit and the good keeping quality for local, dessert and culinary use, having in addition good resistance to bacterial spot and definitely non-browning.

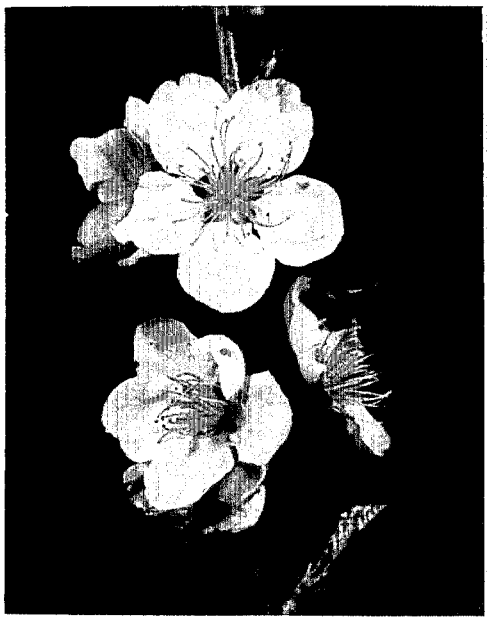
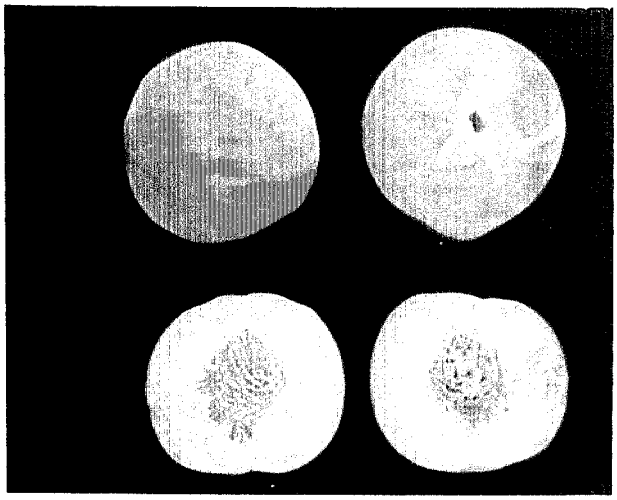

* * * * *